(12) United States Patent
McDonnell

(10) Patent No.: US 8,267,967 B2
(45) Date of Patent: Sep. 18, 2012

(54) METHODS AND APPARATUS FOR MODULAR AND VARIABLE SPINAL FIXATION

(75) Inventor: Christopher McDonnell, Sandy Hook, CT (US)

(73) Assignee: Stryker Spine (FR)

(*) Notice: Subject to any disclaimer, the term of this patent is extended or adjusted under 35 U.S.C. 154(b) by 1032 days.

(21) Appl. No.: 11/304,354

(22) Filed: Dec. 15, 2005

(65) Prior Publication Data
US 2006/0142760 A1    Jun. 29, 2006

Related U.S. Application Data

(60) Provisional application No. 60/636,185, filed on Dec. 15, 2004.

(51) Int. Cl.
*A61B 17/70* (2006.01)
(52) U.S. Cl. ......... 606/254; 606/264; 606/257; 606/259
(58) Field of Classification Search .................. 606/254, 606/259, 260, 261, 262, 246–253, 255–258, 606/263–279; 403/229
See application file for complete search history.

(56) References Cited

U.S. PATENT DOCUMENTS

| | | | | |
|---|---|---|---|---|
| 5,180,393 A | * | 1/1993 | Commarmond | 623/13.14 |
| 5,672,175 A | * | 9/1997 | Martin | 606/86 A |
| 7,377,921 B2 | * | 5/2008 | Studer et al. | 606/86 R |
| 7,785,325 B1 | * | 8/2010 | Milbank | 606/62 |
| 2002/0026193 A1 | * | 2/2002 | Barker et al. | 606/61 |
| 2004/0236327 A1 | * | 11/2004 | Paul et al. | 606/61 |
| 2004/0236328 A1 | | 11/2004 | Paul et al. | |
| 2004/0267260 A1 | * | 12/2004 | Mack et al. | 606/61 |
| 2005/0065516 A1 | * | 3/2005 | Jahng | 606/61 |
| 2005/0085815 A1 | * | 4/2005 | Harms et al. | 606/61 |
| 2005/0203519 A1 | * | 9/2005 | Harms et al. | 606/61 |
| 2006/0009768 A1 | * | 1/2006 | Ritland | 606/61 |
| 2006/0064090 A1 | * | 3/2006 | Park | 606/61 |
| 2006/0184171 A1 | * | 8/2006 | Biedermann et al. | 606/61 |
| 2006/0229612 A1 | * | 10/2006 | Rothman et al. | 606/61 |
| 2008/0177316 A1 | * | 7/2008 | Bergeron et al. | 606/254 |
| 2008/0312694 A1 | * | 12/2008 | Peterman et al. | 606/257 |
| 2009/0182378 A1 | * | 7/2009 | Choi | 606/254 |
| 2010/0042154 A1 | * | 2/2010 | Biedermann et al. | 606/254 |

FOREIGN PATENT DOCUMENTS

| | | |
|---|---|---|
| EP | 0 677 277 A | 10/1995 |
| WO | WO/03/047442 * | 6/2003 |

OTHER PUBLICATIONS

Internationa Search Report, PCT/US2005/045526, Dated Apr. 7, 2006.

* cited by examiner

*Primary Examiner* — Eduardo C Robert
*Assistant Examiner* — Jan Christopher Merene
(74) *Attorney, Agent, or Firm* — Lerner, David, Littenberg, Krumholz & Mentlik, LLP

(57) ABSTRACT

A system and method for the stabilization of the human spine using rods or plates having variable shapes and mechanical properties over their length. The rods or plates may be made up of various segments, each having different properties such as different flexibilities.

14 Claims, 1 Drawing Sheet

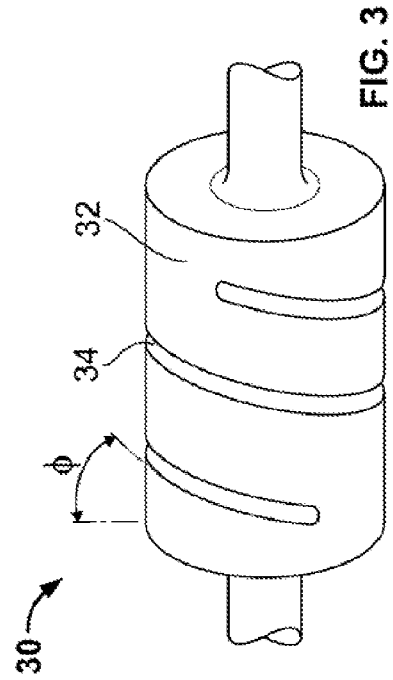
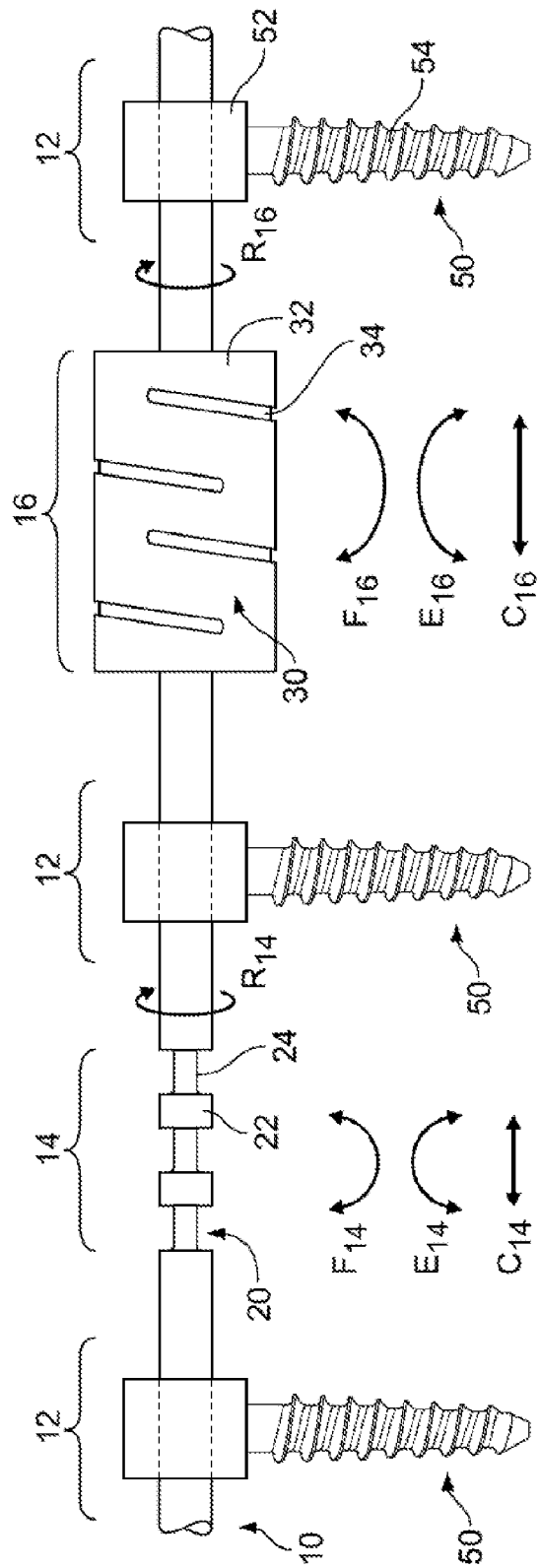
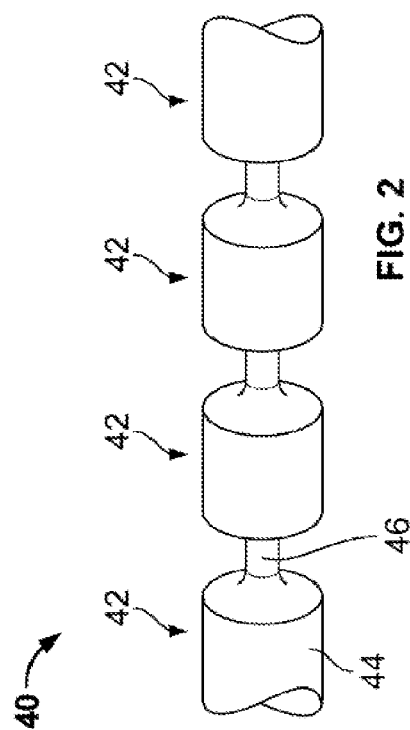

METHODS AND APPARATUS FOR MODULAR AND VARIABLE SPINAL FIXATION

CROSS REFERENCE TO RELATED APPLICATIONS

The present application claims benefit of the filing date of U.S. Provisional Patent Application No. 60/636,185 filed Dec. 15, 2004, the disclosure of which is hereby incorporated herein by reference.

BACKGROUND OF THE INVENTION

The present invention relates to spinal rods and plates used in the stabilization of the human spinal column, and more specifically, to rods and plates that have variable shapes and mechanical properties over their lengths.

Spinal stabilization generally refers to fixation of the spinal column for the purpose of allowing fractured, compressed, or otherwise injured vertebra to heal, or for correction of malformed spinal curvatures. One method of spinal stabilization is to attach rigid rods or plates posteriorly and bilaterally to the spinal column to maintain vertebrae in a desired spatial relationship, or bring vertebrae into a desired curvature. Rods extend over at least two vertebra, and commonly over multiple vertebra, and are affixed to the spinal column using various means such as screws, wires, clamps, or combinations thereof. Plates also typically extend over at least two vertebra, but are more commonly affixed to the spine using screws.

Commonly, spinal rods are cylindrical, and have one consistent cross-section throughout their lengths. Absent a variation in materials within a rod, the size of the cross-section determines the strength of the rod.

However, in spinal surgery, a rod having a consistent cross-section, and therefore consistent mechanical properties throughout its length, is not always desirable. Generally, the loading differs at various spinal segments along the spine. Thus, a target location to be fixed may require application of different forces to improve the overall healing process. For example, it may be desirable for a lumbar segment of the rod to be more rigid than a thoracic segment.

Additionally, because of the change in the amount of space between the spinal column and the dermal tissue of a human back, from more space in the lumbar region to less space at the cervical region, the selection of the desired cross-sectional size of the rod is, in part, controlled by the amount of space available for its implantation. Thus, if a spinal rod that spans several cervical and thoracic vertebrae is desired to be of a certain cross-sectional size and strength for the thoracic region, and if that size is too large to implant into the cervical region, a smaller sized rod would have to be used. This would result in having an undesirably weaker rod fixing vertebra that would benefit more from a stronger, larger rod. This holds true for spinal plates as well.

Thus, there remains a need for rod and plate designs with improved variability and control of mechanical properties, as well as rods and plates that allow a surgeon to select the different mechanical properties that are desired along the rod or plate, and where those mechanical properties should be located. There also remains a need for implantation procedures that facilitate pre-operative or interoperative planning to provide rigidity and flexibility at desired locations.

SUMMARY OF THE INVENTION

An aspect of the present invention is to provide a fixation member such as a rod, plate or other fixation device having modularity and variation in size and/or mechanical properties. Such a fixation member may be constructed as a single unit, or as a modular construct that may be assembled by a surgeon either preoperatively or intraoperatively. While the following discusses spinal rods, it is contemplated that the concepts underlying the devices, systems and methods of the present invention apply also to plates or other members that are connected to the vertebrae in order to fuse or adjust spinal segments. Additionally, it is recognized that these concepts may likewise be applied to other bones and joints such as, but not limited to, femurs, tibias, and other long bones.

A variable spinal rod gets attached to the spine via conventional techniques well known to those skilled in the art, such as via bone screws or hooks. See, for instance, U.S. Pat. No. 6,261,287 (issued Jul. 17, 2001 and entitled "Apparatus for bracing vertebrae"); U.S. Pat. No. 6,217,578 (issued Apr. 17, 2001 and entitled "Spinal cross connector"); U.S. Pat. No. 6,565,565 (issued May 20, 2003 and entitled "Device for securing spinal rods"); U.S. Pat. No. 6,875,211 (issued Apr. 5, 2005 and entitled "Apparatus for spinal stabilization"); and U.S. Pat. No. 6,488,681 (issued Dec. 3, 2002 and entitled "Pedicle screw assembly"). See also U.S. Patent Application Publication Nos. 2003/005426A1 (filed Mar. 20, 2003) and 2002/0133154A1 (filed Sep. 19, 2002), the entire disclosures of which are incorporated herein by reference as if fully set forth herein such that features therein are applicable to the devices, systems, and methods herein. The rod may be attached at the lumbar, thoracic or cervical areas of the spine.

The variable mechanical properties of a spinal rod can be predetermined and selected to provide for micro-motion in order to place a specific load in the area of an intervertebral space, thus encouraging bone growth towards fusion. Additionally, such rods may be used to develop transition zones, where a less than fully rigid system is desirable. Thus, a gradual change in loading along a rod can be built into a fixation system in order to retard the degenerative process on either side of the target zone at which vertebral bodies will be fused. In such a case, the various degrees of rigidity can be selected so that the vertebral segments adjacent those in the target area—i.e., those to be fused—are dynamically stabilized. The load and attendant stresses on those adjacent vertebral segments can be decreased so as to preserve the integrity of those adjacent vertebral segments. As a result, the degeneration of such adjacent vertebral segments can be controlled by a rod or plate system in accordance with the present invention or a method in accordance with the present invention.

Alternatively, the mechanical properties of a variable spinal rod may be adjusted post-operation in response to a patient's post-surgical progress. Thus, if desired, a portion or portions of a variable spinal rod may be adjusted to exert more or less force, or be more or less rigid at corresponding levels of the spinal column where such change is desirable. This may be accomplished, for example, by replacing a rigid segment of a modular construct rod with a variable segment, or adjusting a variable segment of either a unitary or modular construct rod to increase or decrease its stiffness.

In a modular construct rod, various mechanical connections and connection configurations may be employed to enable a surgeon to readily connect the segments of the rod. These connections provide for ease of use as well as speed, strength and reliability. For example, each segment may be designed with male and female portions so that they may be snap-connected to each other. Alternatively, the segments may be threaded and screwed together. Other connections are also envisioned.

The segments of a unitary rod or modular construct rod may alternate between a uniform property segment and a variable property segment, although any sequence of segments is envisioned.

The uniform segments of a rod may differ among themselves in materials, material properties, and sizes. For example, one uniform segment may be of a larger diameter and higher stiffness than another. Alternatively one segment may be of a hollow cross-section, while another may be solid. Still further, one segment may have a circular cross-section, while another may have a square cross-section. These segments may all be arranged together to form a spinal rod.

The variable segments of a rod may offer different mechanical properties through their differing geometries, but also through their material properties. For example, a variable segment may be of cylindrical shape, either hollow or solid, and have radial slots to provide a measure of rotation, flexion, extension, and axial compression. The magnitude of each of these mechanical properties may be controlled by the material properties of the segment, such as for example, using a stiffer titanium "Ti64" versus a less stiff commercially pure titanium, as well as the relative geometries of the slots and solid sections. In conjunction with the material properties of a segment, the rigidity or flexibility of a segment can also be established through treatment or processing of such segment, such as for example, tempering, annealing, surface hardening, and other processes that are well known in the metallurgical arts. Such treatment or processing can be predetermined as custom or prescribed by a surgeon for particular indications.

Apart from the variable segment of cylindrical shape as described above, another variable segment may be in the shape of a two-step cylinder having a larger diameter portion and a smaller diameter portion. Multiple such variable segments may be assembled together end to end, and then coupled to uniform property segments in order to achieve a spinal rod that will have the desired mechanical properties in the desired locations on the rod.

In one aspect the present invention comprises a method of spinal fixation comprising including inserting a plurality of screws into at least three vertebral bodies of a spine such that the screws open at least two disc spaces, providing a spinal rod having a plurality of segments that exhibit different properties of flexibility, and connecting the spinal rod to the plurality of screws in such a manner that the rod spans the at least two disc spaces whereby at least one disc space is associated with a segment of the rod having a different degree of flexibility than at least one other segment of the rod as associated with another disc space.

Another aspect of the present invention is a method of assembling a modular construct spinal rod having variable mechanical properties by selectively joining uniform property segments and variable property segments to form the rod. In a particular spinal fixation procedure, a method in accordance with the present invention includes determining which mechanical forces should be applied to the spine, and where they should be applied. A modular spinal rod may be constructed by selecting from appropriate uniform property segments and variable property segments, and joining them together so that the different sections of the rod correspond to the predetermined positions on the spine where the different forces are to be applied.

The method of implanting a variable spinal rod includes arranging the rod in the appropriate location in order to facilitate use of the variable property segments, whether the rod is a modular or unitary rod having different mechanical properties along its length. A full implantation procedure, including pedicle screws, hooks or any other known procedure, can then be performed. By way of example, it may be determined that a long spinal rod is required which will span the thoracic region of the spine. If the middle of the thoracic region should ideally be allowed to have less flexibility than the ends, then a spinal rod may be constructed by assembling a rigid, uniform property segment, with variable property segments in the shapes of slotted cylinders on either end, to achieve the ultimate desired rod length and properties.

Another aspect of the present invention is a system that includes fixation devices such as screws or hooks, and rods that have segments with variable rigidity or flexibility, the rods being either one-piece integral rods or modular rods, as explained herein.

In another aspect the present invention is a pedicle screw system including a spinal rod. The spinal rod preferably comprises a lower segment having a lower cross-section, an intermediate segment in communication with said lower segment having an intermediate cross-section and an axis, and an upper segment in communication with said intermediate segment with an upper cross-section. At least one of the segments has a different degree of flexibility than at least one of said other segments. The system also includes at least three fasteners associated with rod-receiving coupling elements for receiving said spinal rod. The fasteners, the rod-receiving coupling elements, and the rods are fixable together. In one aspect, the fasteners are associated with said rod-receiving coupling elements to allow for polyaxial movement of said rod-receiving coupling elements prior to being fixed together with the spinal rod.

In addition to the above, other aspects of the present invention include devices such as systems and methods that utilize an intervertebral spacer or fusion device in addition to fixation members such as rods or plates. Thus, an intervertebral device such as a cage or a bone graft can be utilized in connection with a fixation system having rods or plates with variable property segments such that the rigidity or flexibility of a rod or plate can be varied in connection with the use of the intervertebral device. Intervertebral devices such as those disclosed in U.S. Pat. Nos. 4,961,740 and 5,906,616 are contemplated, and the entire disclosures of such patents are incorporated herein by reference as if fully set forth herein.

It is also contemplated that a rod, plate or other fixation system that has variable rigidity or flexibility built into the devices can be utilized in connection with an artificial disc to be implanted in an intervertebral space. Such fixation devices can be used in connection with a system and/or method by which such fixation devices are on one or both sides of the artificial disc, either at one level above or below, or more than one level above or below the artificial disc in order to stabilize to some degree vertebral bodies that are directly adjacent or remotely adjacent to the artificial disc.

While such a system can be developed with segments having variable rigidity, constant rigidity can be built into the fixation devices on either side of the artificial disc. Variability can differ on either side of an artificial disc, or, alternatively, one side of the artificial disc can receive a fixation device that has a constant stiffness while the other side can receive a fixation device that has variable stiffness. Alternatively, the fixation devices on one or both sides of the artificial disc can provide for less rigidity than would normally be provided in the use of fixation devices towards stabilization or fusion, perhaps to provide a flexible attachment that allows for motion or micro-motion, though some degree of stabilization would be provided. Artificial discs such as those shown in published U.S. application Ser. No. 10/382,702 to Zubok et al., entitled "Cervical disc replacement" and published U.S.

application Ser. No. 10/256,160 to Errico et al., entitled "Artificial intervertebral disc having limited rotation using a captured ball and socket joint with a solid ball and compression locking post" can be used in such systems and/or methods, and the entire disclosure of such patents are incorporated herein by reference as if fully set forth herein.

BRIEF DESCRIPTION OF THE DRAWINGS

FIG. 1 is a perspective view of a variable spinal rod connected to bone fixation members, the rod having two sections of different mechanical properties.

FIG. 2 is a perspective view of several variable segments of a variable spinal rod connected together.

FIG. 3 is a perspective view of one variable segment in the form of a radially slotted cylinder.

DETAILED DESCRIPTION OF THE DRAWINGS

FIG. 1 illustrates a variable spinal rod 10 of the present invention. The rod 10 is comprised of several uniform rod segments 12 as well as variable rod segments 14 and 16. The rod 10 may either be a manufactured single unit, or a modular construct where the various segments 12, 14 and 16 have been assembled together. Assembly may be performed by a surgeon, either preoperatively or intraoperatively, for example.

The rod 10 is attached to fixation members 50 which anchor the rod 10 to the spine, as is well known in the art. Fixation members 50 have a rod capturing portion, or body 52, which houses the rod 10, and a treaded portion, or shank 54, which is threaded into a portion of a spinal vertebra. As is well known in the art, fixation members 50 may be of any other form that is suitable for attaching a spinal rod to the spine. For example, one or more of the fixation members 50 may be hooks that connect to the spine by hooking to the lamina rather than getting screwed into the bone.

As illustrated in FIG. 1, variable segment 14 is a block segment 20 that is made up of alternating larger 22 and smaller 24 square-shaped sections. With such geometry, it is known that variable segment 14 will have certain rotation $R_{14}$, flexion $F_{14}$, extension $E_{14}$, and axial compression $C_{14}$ properties that will be different from those of adjacent uniform segments 12.

With additional reference to FIG. 3, variable segment 16 is a slotted segment 30 in the shape of a cylinder having alternating solid sections 32 separated by radial slots 34. The slots may be oriented at any angle Ø, which will have an effect on the mechanical properties of the segment 30. With such geometry, it is known that variable segment 16 will have certain rotation $R_{16}$, flexion $F_{16}$, extension $E_{16}$, and axial compression $C_{16}$ properties that will be different from those of adjacent uniform segments 12, as well as from those of variable segment 14.

FIG. 2 illustrates a modular construct portion 40 of a variable spinal rod 10. Portion 40 is assembled from four segments 42. Each segment 42 has a larger diameter portion 44 which transitions to a smaller diameter portion 46. The segments 42 are assembled end to end such that portion 46 of one segment attaches to portion 44 of another segment. Numerous connection mechanisms may be employed to facilitate connecting segments 42, so long as these mechanisms are reliable and do not undesirably disconnect or otherwise fail in use. Modular construct portion 40 may further be connected to uniform rod segments, such as segments 12, on either of its ends, and thus form a variable spinal rod 10.

It is understood that numerous variations of rod or plate segment shapes, sizes and material properties may be formed and used alone or together with intervertebral devices as planned preoperatively or intraoperatively. These can be combined to create the desired variable spinal rod or plate system. However, although the present invention has been described with reference to the particular embodiments herein, it is not intended that the invention be limited thereto, as it is intended that the invention be as broad in scope as the art will allow and that the specification be read likewise. It will therefore be appreciated by those skilled in the art that yet other modifications could be made to the invention without deviating from its spirit and scope as so claimed.

The claims presented herein are a non-exhaustive list, and are presented in addition to, and in conjunction with, what is described in the Summary of the Invention.

IDENTIFICATION OF ELEMENT NUMBERS

| | |
|---|---|
| 10 | Spinal Rod |
| 12 | uniform property segment of the rod |
| 14 | variable property segment of the rod |
| 16 | variable property segment of the rod |
| 20 | Block Segment |
| 22 | larger sections |
| 24 | smaller sections |
| 30 | Slotted Segment |
| 32 | solid sections |
| 24 | slots |
| 40 | Modular Construct portion of a variable spinal rod |
| 42 | segment |
| 44 | larger diameter portion |
| 46 | smaller diameter portion |
| 50 | Fixation Members |
| 52 | rod capturing portion/Body |
| 54 | threaded portion/Shank |
| $R_{14}$ | rotation |
| $F_{14}$ | flexion |
| $E_{14}$ | extension } For segment 14 of the rod |
| $C_{14}$ | axial compression |
| $R_{16}$ | rotation |
| $F_{16}$ | flexion |
| $E_{16}$ | extension } For segment 16 of the rod |
| $C_{16}$ | axial compression |
| Ø | angle of radial slots of slotted segment 30 |

The invention claimed is:

1. A spinal rod assembly comprising:
first, second, and third uniform rod segments;
a lower segment in communication with the first and second uniform rod segments;
an upper segment in communication with the second and third uniform rod segments;
wherein the lower segment and the upper segment differ from each other and from the uniform rod segments in at least one of shape and material properties so that the lower segment and the upper segment have different flexibilities from each other and from the uniform rod segments,
wherein the stiffness of each of the lower and upper segments is constant, and
wherein at least one of the lower and upper segments is a block segment made up of alternating larger and smaller square-shaped sections.

2. The spinal rod of claim 1, wherein one of the rod segments has a cross-section which is smaller or larger than cross-sections of the lower and upper segments.

3. The spinal rod of claim 1, wherein at least one of the lower and upper segments includes at least one annular slit.

4. The spinal rod of claim 3, wherein the at least one annular slit is at an angle to a plane that is transverse to the axis.

5. The spinal rod of claim 1, wherein at least one of the lower and upper segments includes a peripheral spiraled slit.

6. The spinal rod of claim 1, wherein at least one of the lower and upper segments includes two peripherally spiraled slits.

7. The spinal rod of claim 1, wherein each of the first, second, and third uniform rod segments has a substantially similar cross-section.

8. A method of spinal fixation, comprising:
   inserting a plurality of screws into at least three vertebral bodies of a spine;
   providing a spinal rod having an elongated body having at least two segments, wherein each segment has a flexible component between two uniform rod portions, each flexible component having a different flexibility than the flexible component of at least one other segment, wherein at least one of the flexible components is a block segment made up of alternating larger and smaller square-shaped sections; and
   connecting the spinal rod to the plurality of screws in such a manner that the rod spans the at least two disc spaces whereby at least one disc space is associated with a one of the at least two segments of the rod having a flexible component having a different degree of flexibility than the flexible component of another of the at least one two other segments of the rod as associated with another disc spac,
   connecting the spinal rod to the plurality of screws in such a manner that the rod spans at least two disc spaces whereby at least one disc space is associated with one of the at least two segments and another of the at least two disc spaces is associated with another of the at least two segments.

9. The method of claim 8 wherein the the at least two segments each have different axial compression properties.

10. A pedicle screw system comprising:
    (a) a spinal rod assembly including:
        (i) first, second, and third uniform rod segments;
        (ii) a lower segment in communication with the first and second uniform rod segments; and
        (iii) an upper segment in communication with the second and third uniform rod segments;
    wherein the lower segment and the upper segment differ from each other and from the uniform rod segments in at least one of shape and material properties so that the lower segment and the upper segment have different flexibilities from each other and from the uniform rod segments, and wherein the stiffness of each of the lower and upper segments is constant; and
    (b) at least three fasteners with rod-receiving coupling elements for receiving the spinal rod assembly;
    wherein the fasteners, the rod-receiving coupling elements, and the rod segments are fixable together, and
    wherein at least one of the lower and upper segments includes a plurality of tapered segments having a larger diameter portion that transitions to a smaller diameter portion, the tapered segments being assembled such that the smaller diameter portion of one tapered segment attaches to the larger diameter portion of another segment.

11. The system of claim 10 wherein the at least three fasteners are associated with the rod-receiving coupling elements to allow for polyaxial movement of the rod-receiving coupling elements prior to being fixed together with the spinal rod assembly.

12. The system of claim 10, wherein each of the first, second, and third uniform rod segments has a substantially similar cross-section.

13. A spinal rod, comprising:
    an elongated body having at least two segments, wherein each segment has a flexible component between two uniform rod portions, each flexible component having a different flexibility than the flexible component of at least one other segment,
    wherein at least one of the flexible components is a block segment made up of alternating larger and smaller square-shaped sections.

14. The system of claim 13, wherein each of the uniform rod portions has a substantially similar cross-section.

* * * * *

UNITED STATES PATENT AND TRADEMARK OFFICE
CERTIFICATE OF CORRECTION

Page 1 of 1

PATENT NO.         : 8,267,967 B2
APPLICATION NO.    : 11/304354
DATED              : September 18, 2012
INVENTOR(S)        : Christopher McDonnell It is certified that error appears in the above-identified patent and that said Letters Patent is hereby corrected as shown below:

In the Claims:

Column 7, lines 23 through lines 30, please delete the paragraph "connecting the spinal rod to the plurality of screws in such a manner that the rod spans the at least two disc spaces whereby at least one disc space is associated with a one of the at least two segments of the rod having a flexible component having a different degree of flexibility than the flexible component of another of the at least one two other segments of the rod as associated with another disc spac,"

Column 7, line 37, please delete the word "the" after the word "the"

Signed and Sealed this
Sixth Day of May, 2014

Michelle K. Lee
*Deputy Director of the United States Patent and Trademark Office*